United States Patent
Lewis

(10) Patent No.: US 9,237,971 B2
(45) Date of Patent: Jan. 19, 2016

(54) TAMPON SKIRT

(71) Applicant: Cathy Lewis, El Paso, TX (US)

(72) Inventor: Cathy Lewis, El Paso, TX (US)

( * ) Notice: Subject to any disclaimer, the term of this patent is extended or adjusted under 35 U.S.C. 154(b) by 235 days.

(21) Appl. No.: 13/901,843

(22) Filed: May 24, 2013

(65) Prior Publication Data

US 2014/0350451 A1    Nov. 27, 2014

(51) Int. Cl.
*A61F 13/20*    (2006.01)
*A61F 13/26*    (2006.01)

(52) U.S. Cl.
CPC ............... *A61F 13/208* (2013.01); *A61F 13/26* (2013.01); *A61F 13/20* (2013.01); *A61F 13/2071* (2013.01)

(58) Field of Classification Search
CPC .... A61F 13/20; A61F 13/2071; A61F 13/208
USPC ................. 604/385.02, 385.17, 385.18, 904
See application file for complete search history.

(56) References Cited

U.S. PATENT DOCUMENTS

| | | | | |
|---|---|---|---|---|
| 3,946,737 A | * | 3/1976 | Kobler | 604/385.18 |
| 5,891,123 A | * | 4/1999 | Balzar | 604/385.18 |
| 2003/0097108 A1 | * | 5/2003 | Hasse et al. | 604/379 |
| 2005/0015041 A1 | | 1/2005 | Karapasha | |
| 2007/0118067 A1 | | 5/2007 | Lamb | |
| 2009/0192436 A1 | | 7/2009 | Karapasha et al. | |

* cited by examiner

*Primary Examiner* — Jacqueline Stephens
(74) *Attorney, Agent, or Firm* — Luis M. Ortiz; Kermit D. Lopez; Ortiz & Lopez, PLLC

(57) ABSTRACT

A tampon skirt is disclosed. The tampon skirt can comprise a finger cover associated with the tampon that expands or opens when a user unwraps a tampon, or an integrated tampon wrapper/cover that expands or opens when a user unwraps a tampon. The tampon skirt is associated with a tampon and conforms around a surface of the tampon. The cover is deployable to cover a finger of a user when the user prepares to insert the tampon. The user's grips the withdrawal end underneath the extended tampon skirt when the user is inserting the tampon. The tampon skirt is appropriately sized to cover a user's fingers and/or hand to prevent contact with menstrual discharge. When the user finishes inserting the tampon with the associated tampon skirt, the user disposes of the remaining tampon applicator and associated tampon skirt.

16 Claims, 4 Drawing Sheets

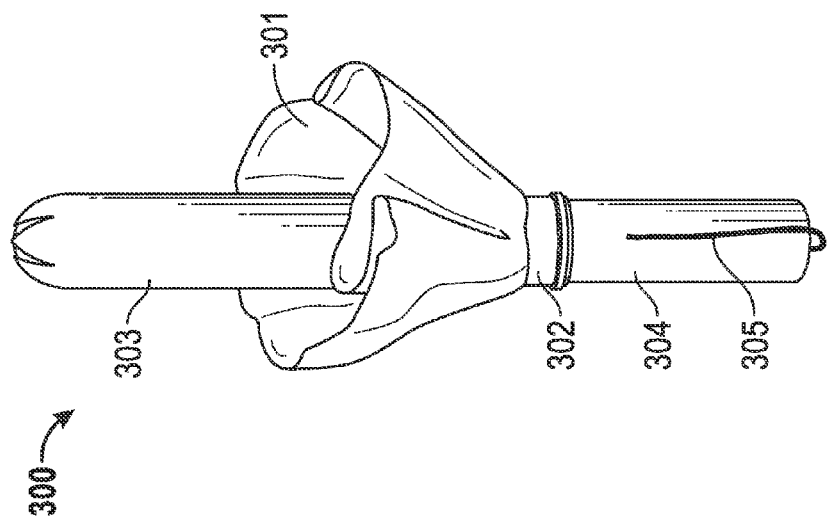
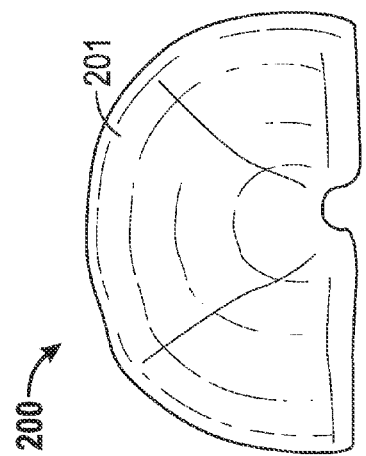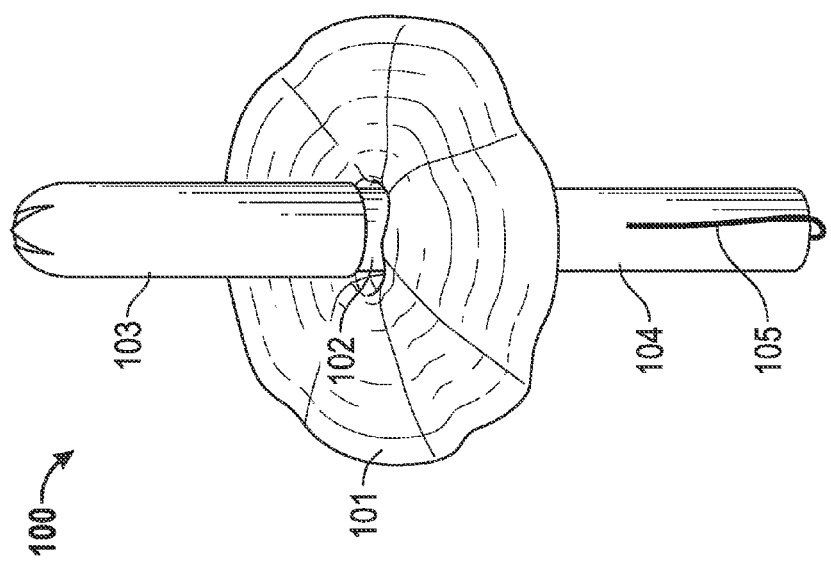

TAMPON SKIRT

CROSS REFERENCE TO RELATED APPLICATIONS

This patent application claims the benefit under 35 U.S.C. §119(e) of U.S. Provisional Patent Application Ser. No. 61/705,224 filed on Sep. 25, 2012 and entitled "TAMPON COVER," which is hereby incorporated by reference in its entirety.

FIELD OF THE INVENTION

The disclosed embodiments relate to tampons. The disclosed embodiments further relate to an improved tampon skirt. The disclosed embodiments also relate to a tampon skirt that expands to cover a user's finger(s) and/or hand during insertion of the tampon.

BACKGROUND

Tampons generally refer to any type of absorbent structure for insertion into the vaginal canal or other body cavities for absorption of fluid or gas. Typically configured with an insertion end, a withdrawal end, a length, a width, a longitudinal axis, and a radial axis, a tampon may be compressed into a generally cylindrical configuration in the radial direction, axially along the longitudinal axis or in both the radial and axial directions. A tampon's length is measured from the insertion end to the withdrawal end along the longitudinal axis, with exemplary dimensions measuring 30-60 mm long and 8-20 mm wide. A tampon may be straight or non-linear in shape such as curved along the longitudinal axis. Tampons are generally tightly packed in individual wrappers for easy carrying and protection of the tampon from the environment prior to use.

When a tampon is inserted by hand, however, the user risks contaminating their fingers and/or nails with menstrual discharge during insertion. Accordingly, there exists a need for an improved tampon skirt with improved ease of deployment to cover a user's fingers, nails, or hand when inserting a tampon to promote clean and hygienic insertion.

SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is therefore an object of the disclosed embodiments to provide for improved tampons.

It is another object of the disclosed embodiments to provide for an improved tampon skirt.

It is an additional object of the disclosed embodiments to provide an improved tampon skirt that expands to cover a user's finger and/or hand.

The above and other aspects can be achieved as is now described. A tampon skirt is disclosed. The tampon skirt can comprise a finger cover associated with the tampon that expands or opens when a user unwraps a tampon, or an integrated tampon wrapper/cover that expands or opens when a user unwraps a tampon. The tampon skirt is associated with a tampon and conforms around a surface of the tampon. The cover is deployable to cover a finger of a user when the user prepares to insert the tampon. The user's grips the withdrawal end underneath the extended tampon skirt when the user is inserting the tampon. The tampon skirt is appropriately sized to cover a user's fingers and/or hand to prevent contact with menstrual discharge. When the user finishes inserting the tampon with the associated tampon skirt, the user disposes of the remaining tampon applicator and associated tampon skirt.

BRIEF DESCRIPTION OF THE FIGURES

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

FIG. 1 illustrates an exemplary pictorial illustration of a tampon skirt attached to a tampon, according to a preferred embodiment;

FIG. 2 illustrates an exemplary pictorial illustration of a tampon skirt, according to an embodiment;

FIG. 3 illustrates an exemplary pictorial illustration of a tampon skirt attached to a tampon, according to an embodiment;

DETAILED DESCRIPTION

Figure 4A:
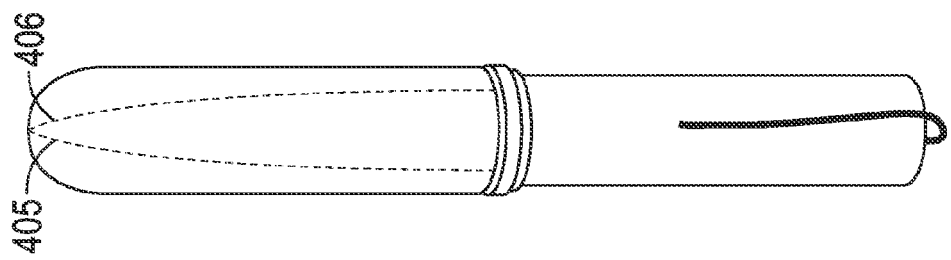
FIGS. 4a-4e illustrate exemplary lines of weakness in the tampon skirt, according to an embodiment.
Figure 4B:
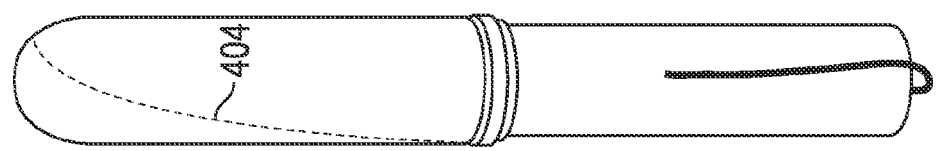
Figure 4C:
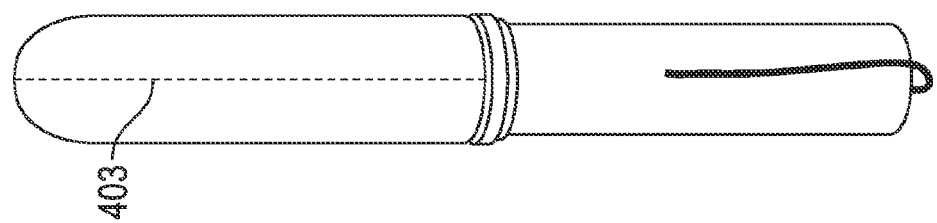
Figure 4D:
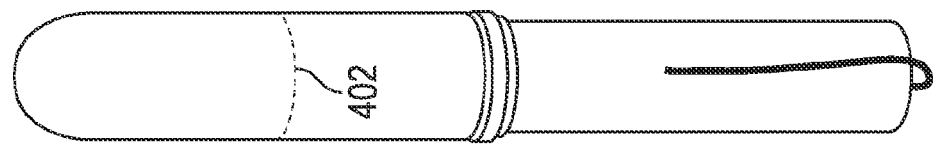
Figure 4E:
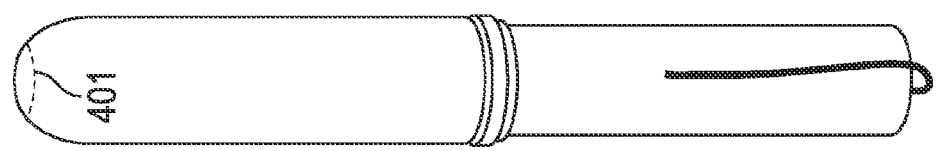

The particular values and configurations discussed in these non-limiting examples can be varied and are cited merely to illustrate at least one embodiment and are not intended to limit the scope thereof.

The embodiments will now be described more fully hereinafter with reference to the accompanying drawings, in which illustrative embodiments of the invention are shown. The embodiments disclosed herein can be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. As used herein, the term "and/or" includes any and all combinations of one or more of the associated listed items.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 illustrates an exemplary pictorial illustration 100 of a tampon skirt 101, also known as a tampon cover or tampon finger cover, attached to a tampon 102, according to a preferred embodiment. The tampon skirt 101 can comprise a finger cover associated with the tampon 102 that expands or opens when a user unwraps a tampon, or an integrated tampon wrapper/cover that expands or opens when a user unwraps a tampon. The tampon skirt 101 is associated with a tampon 102 and conforms around a surface of the tampon 102. The skirt 101 is deployable to cover a finger of a user when the user prepares to insert the tampon 102. The user's grips the withdrawal end 104 underneath the extended tampon skirt 101 when the user is inserting the tampon 102. The tampon skirt 101 is appropriately sized to cover a user's fingers and/or hand to prevent contact with menstrual discharge. When the user finishes inserting the tampon with the associated tampon skirt, the user disposes of the remaining tampon applicator and associated tampon skirt 101.

The tampon skirt 101 can be partially associated with the insertion end 103 of the tampon 102 or the withdrawal end 104 of the tampon 102, as is not limited to a particular configuration as illustrated in FIG. 1. The tampon skirt 101 can be formed from any suitable material such as, for example, thin and flexible plastic material. In certain embodiments, the tampon skirt 101 can be formed as an extension of one or more components or of a portion of one or more components of the tampon 102 such as, e.g., the overwrap and/or the absorbent mass. Alternatively, or in addition, the tampon skirt 101 can be added as a separate material and joined to the tampon 102 at any suitable location on the tampon 102. The tampon skirt 101 can comprise a flexible material that is suitably shaped to cover a user's finger. The tampon skirt 101 can open at a line of weakness at an insertion end of said tampon 102 or at a line of weakness bisecting said tampon 102, as illustrated in FIGS. 4a-4e. The tampon skirt 101 can also be supported in an opened position via a support member illustrated in FIGS. 5 and 6 associated with the tampon skirt 101.

To use the tampon 102 and associated tampon skirt 101, the user unfurls the tampon skirt 101 to cover the user's finger and/or hand. The user then positions the first end of the insertion end 103 of the tampon 102 appropriately, grasps the insertion member 103, and moves the plunger in the insertion member 103 towards the user's body to insert the tampon 102. A tampon 102 includes an applicator with an insertion member 103 adapted to house an absorbent tampon and receive a plunger, or withdrawal end 104. The tampon insertion member 103 has a first end for insertion of the tampon 102 and a second end for receipt of the plunger, and a tampon withdrawal cord 105. Some applicators also include a fingergrip configuration located on the insertion member 103, which allows the consumer to more securely hold the applicator during insertion of a material into the body cavity.

As used herein, the term "tampon" refers to any type of absorbent structure that is inserted into the vaginal canal or other body cavities for the absorption of fluid and/or gas therefrom, to aid in wound healing, or for the delivery of active materials such as medicaments or moisture. The tampon may be compressed into a generally cylindrical configuration in the radial direction, axially along the longitudinal axis or in both the radial and axial directions. While the tampon may be compressed into a substantially cylindrical configuration, other shapes are possible. These may include shapes having a cross section that may be described as rectangular, triangular, trapezoidal, semi-circular, hourglass, serpentine, or other suitable shapes. The disclosed embodiments can be embodied in any type of tampon (e.g., digital tampon, catamenial tampon, applicator tampon, etc.). Catamenial tampons are typically inserted into a vagina of a woman to absorb menstrual discharges during menstruation. The term "digital tampon" refers to a tampon which is intended to be inserted into the vaginal canal with the user's finger and generally without the aid of an applicator.

FIG. 2 illustrates an exemplary pictorial illustration 200 of a tampon skirt 201, according to an embodiment. The tampon skirt 201 can be removable or insertable in any position on the tampon. With a circular hole in the middle of the tampon skirt 201, the user can adjust the position of the tampon skirt to appropriately cover the user's fingers and/or hand when inserting a tampon. The tampon skirt 201 can be sold together with a tampon or separately, for example.

FIG. 3 illustrates an exemplary pictorial illustration 300 of a tampon skirt 301 attached to a tampon 302, according to an embodiment. The tampon skirt 301 and/or the withdrawal cord 305 can be compacted in a suitable manner. The tampon skirt 301 can be compacted around the insertion end 303 of the tampon 302, while the withdrawal cord 305 can be compacted around the withdrawal end 304 of the tampon 302. For example, the tampon skirt 301 and/or withdrawal cord 305 can be folded, rolled, wound, looped, twisted, and/or otherwise compacted such that at least a portion of, a majority of, and/or all of the skirt 301 and/or withdrawal cord 305 can fit in the wrapper or conform around the surface of the tampon. The wrapper can separate into two or more pieces to expose the tampon skirt 301. Alternatively, the tampon skirt 301 alone can function as both the tampon cover and the fingers/hand cover. In FIG. 3, the tampon skirt 301 functions as both the finger cover and tampon wrapper. When wrapped, the user unfurls the tampon wrapper and cuts or rips the tampon skirt 301 at a line of weakness to create a circular cover for the fingers and/or hand.

The tampon skirt 301 and/or tampon wrapper is flushable and comprised of an anaerobically degradable material (e.g., anaerobically degradable thermoplastic polymers are useful in the present invention including, but are not limited to, polyesteramides, polyhydroxyalkoates, and mixtures thereof) that is melt extrudable or moldable such that it can be made into fibers, films, laminates or shaped articles suitable for use in the tampon wrapper and/or tampon skirt 301. The tampon skirt 301 can include one or more materials that can be a nonwoven or film such as, e.g., a nonwoven or film that is fluid impervious and/or fluid repellent. It is desirable that such material has sufficient mechanical properties including the ability to be stretched and/or elongated without structural failures (e.g., tearing, ripping). Suitable wrapper materials include, e.g., polymeric films made of polyethylene, polypropylene, polyester, polystyrene, PET (polyethylenetherephthalate), cellophane, polyimide, polyvinyl chloride), ethylene-vinyl acetate copolymer and the like; synthetic or natural (e.g. rubber) elastomers. The tampon skirt 301 can comprise one or more flexible polymeric films such as, for example, films having a thickness of less than about 1 mm. Tampon skirt 301 and/or wrappers are applied to the tampon using any suitable technique including, for example, heat-shrinking, heat sealing, adhesives, pressure, stretching, lamination, coating, gluing, embossing, crimping, sewing, stitching, entangling, mechanical interlocking, cold pressure welding, ultrasonic bonding, manual placement, and combinations thereof.

FIGS. 4a-4e illustrate exemplary pictorial illustrations of lines of weakness 401, 402, 403, 404, 405, 406 in the tampon skirt 101, 201, 301, according to an embodiment. When the user prepares to insert the tampon, the user unfolds the tampon skirt by opening the tampon skirt at a line of weakness 401, 402, 403, 404, 405, 406 or perforation on the wrapper or tampon skirt. The line of weakness 401, 402, 403, 404, 405, 406 or perforation can be a single line or a plurality of lines at any location on the tampon skirt (e.g., at the topmost portion at the insertion end, bisecting the tampon skirt).

For instance, the line of weakness 401, 402, 403, 404, 405, 406 can only extend around a portion of the wrapped tampon in terms of length and perimeter in order to prevent tearing-off of parts of the tampon skirt upon opening of the wrapper, which could result in fragmentation of the tampon skirt. This opening means can prevent or reduce separation of the tampon skirt into more than one piece of tampon skirt material upon opening of the tampon skirt.

The tampon skirt can have any suitable shape (e.g., round, oval, square, etc.) and dimension(s) to ensure coverage of the user's fingers and/or hand. The line of weakness for opening a tampon skirt can comprise a line of weakness around the first end of the insertion end of the tampon 401, or a line of weakness around the circumference of the middle of the insertion end of the tampon 402. The opening can be vertical to a longitudinal axis in the tampon, for example, straight cut 403, or can be angled to the axis, for example, angled cut 404. The opening can comprise a "rosebloom" appearance 405, 406 wherein the skirt functions as the tampon wrapper as the tampon skirt conforms around the surface of the tampon, preferably around the insertion end. Alternative embodiments can include a separate wrapper to cover the tampon skirt associated with a tampon.

Figure 5:
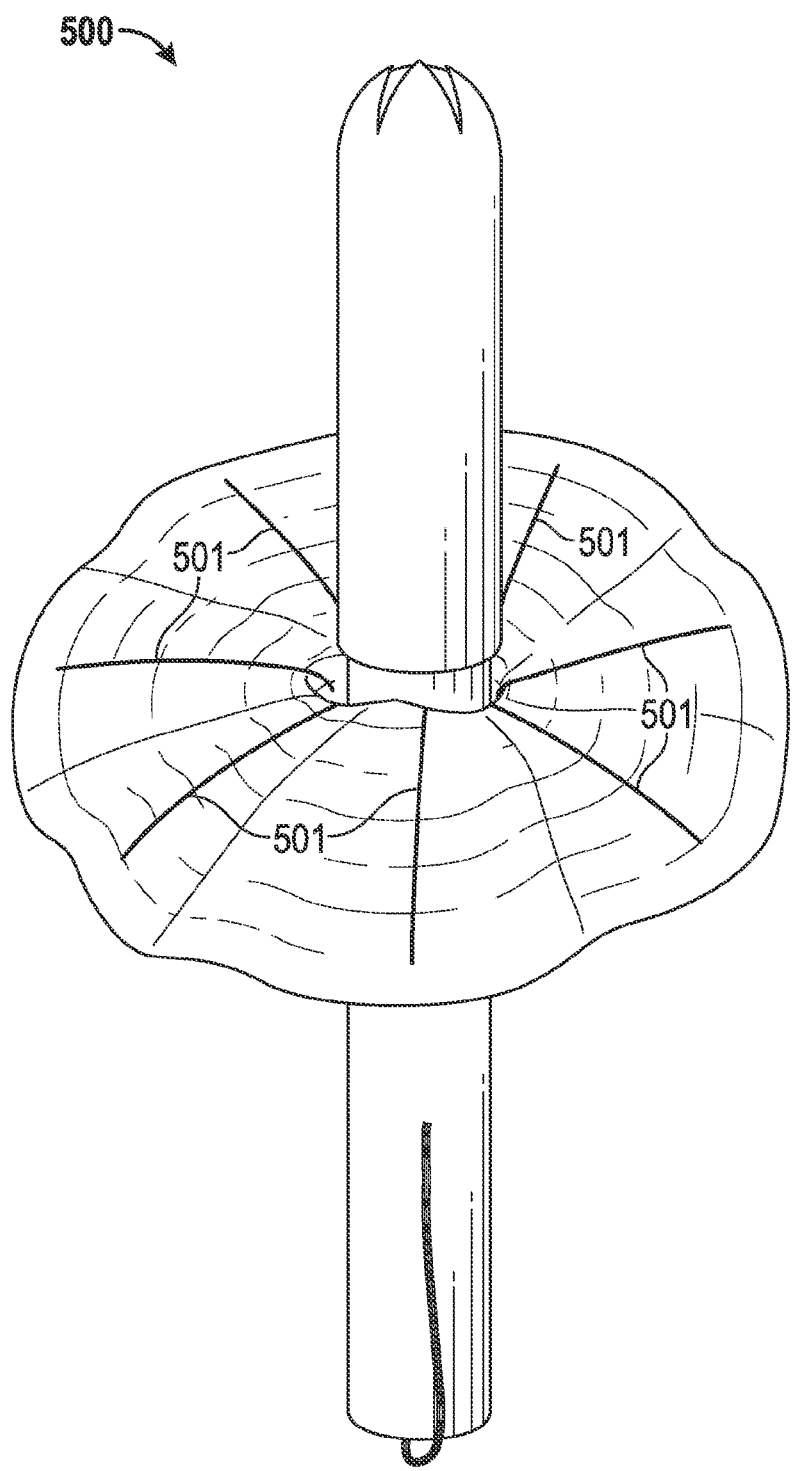
FIG. 5 illustrates an exemplary pictorial illustration of a tampon skirt with associated ribbing to automatically unfurl the tampon skirt, according to an embodiment.

FIG. 5 illustrates an exemplary pictorial illustration 500 of a tampon skirt with associated ribbing 501 to automatically unfurl the tampon skirt, according to an embodiment. When the user prepares to insert the tampon with the tampon skirt, the tampon skirt unfurls automatically or manually with the assistance of ribbing 501. The tampon skirt automatically opens with associated ribbing 501 support structures throughout the skirt. The ribbing 501 extends radially from the tampon, for example. The ribbing 501 can also be used in addition to a support structure lining the perimeter of the tampon skirt.

Figure 6:
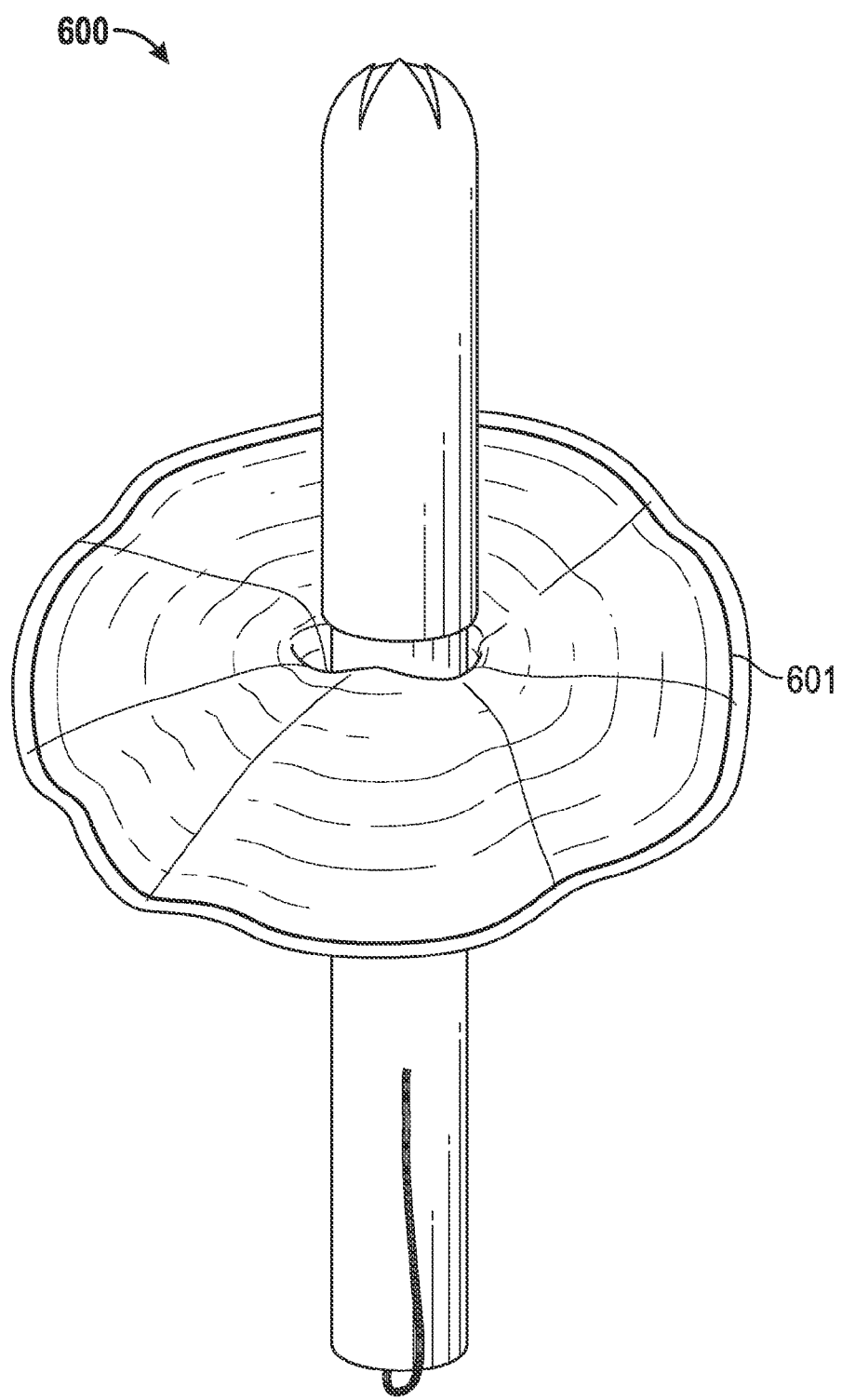
FIG. 6 illustrates an exemplary pictorial illustration of a tampon skirt with an associated ring to automatically unfurl the tampon skirt, according to an embodiment.

FIG. 6 illustrates an exemplary pictorial illustration 600 of a tampon skirt with an associated ring 601 to automatically unfurl the tampon skirt, according to an embodiment. The ring 601 support structure can include, for example, a malleable plastic or rubber ring associated with the perimeter of the tampon skirt. The support ring 601 holds the tampon skirt open and creates a perimeter around the edge of the tampon skirt. The extended tampon skirt barrier can collapse onto itself when the user is inserting the tampon, thus ensuring that fingers remain clean and prevent needless risk.

Based on the foregoing, it can be appreciated that a number of different embodiments, preferred and alternative, are disclosed herein. For example, in one embodiment, a tampon skirt apparatus is disclosed. The tampon skirt apparatus comprises a flexible component attached to a tampon that unfurls to cover at least one finger or hand when inserting a tampon, wherein the flexible component prevents menstrual discharge from contacting the at least one finger or the hand.

In another embodiment, the flexible component attaches to the tampon at an insertion end of the tampon, wherein the flexible component comprises a hole in the middle of the flexible component to attach the flexible component to the insertion end of the tampon. In yet other embodiments, the tampon skirt apparatus further comprises at least one line of weakness in the flexible component, wherein the at least one line of weakness marks a location in the flexible component to open the flexible component to cover the at least one finger or the hand. In yet another embodiment, the tampon skirt apparatus further comprises a wrapper covering the flexible component attached to the tampon, wherein the tampon skirt is compacted around the tampon. In another embodiment, the tampon skirt is compacted around the tampon.

In yet other embodiments, the tampon skirt apparatus further comprises at least one rib associated with the flexible component, wherein the at least one rib automatically unfurls the flexible component and supports the flexible component in an opened position over the at least one finger and the hand. In another embodiment, the tampon skirt apparatus further comprises at least one support ring associated with the flexible component at an edge of the flexible component, wherein the at least one support ring automatically unfurls the flexible component and supports the flexible component in an opened position over the at least one finger and the hand.

In another her embodiment, the flexible component comprises at least one of a round shape, a circular shape, an oval shape, a square shape, and a rosebloom shape. In other embodiments, the flexible component comprises at least one of an anaerobically degradable material, an anaerobically degradable thermoplastic polymers, polyesteramides, polyhydroxyalkoates, a film, a laminate, a shaped article, a plastic material, a fluid impervious film, a fluid repellant film, a nonwoven film, a polymeric films made of polyethylene, polypropylene, polyester, polystyrene, PET (polyethyletherephthalate), cellophane, polyamide, polyvinyl chloride), or ethylene-vinyl acetate copolymer, a synthetic rubber elastomer, a natural rubber elastomers, and a film having a thickness of less than about 1 mm. In yet another embodiment, the tampon comprises at least one of a digital tampon, a catamenial tampon, and an applicator tampon.

In another embodiment, a tampon skirt apparatus is disclosed. The tampon skirt apparatus comprises: a flexible component attached to a tampon that unfurls to cover at least one finger or hand when inserting a tampon, wherein the component prevents menstrual discharge from contacting the at least one finger or the hand, wherein the flexible component attaches to the tampon at an insertion end of the tampon, wherein the flexible component comprises a hole in the middle of the flexible component to attach the flexible component to the insertion end of the tampon, wherein the tampon comprises at least one of a digital tampon, a catamenial tampon, and an applicator tampon.

In one embodiment, the tampon skirt apparatus further comprises at least one line of weakness in the flexible component, wherein the at least one line of weakness marks a location in the flexible component to open the flexible component to cover the at least one finger or the hand. In another embodiment, the tampon skirt is compacted around the tampon.

In yet other embodiments, the tampon skirt apparatus further comprises at least one rib associated with the flexible component, wherein the at least one rib automatically unfurls the flexible component and supports the flexible component in an opened position over the at least one finger and the hand. In another embodiment, the tampon skirt apparatus further comprises at least one support ring associated with the flexible component at an edge of the flexible component, wherein the at least one support ring automatically unfurls the flexible component and supports the flexible component in an opened position over the at least one finger and the hand.

In another embodiment, a tampon skirt apparatus is disclosed. The tampon skirt apparatus comprises: a flexible component attached to a tampon that unfurls to cover at least one finger or hand when inserting a tampon, wherein the flexible component prevents menstrual discharge from contacting the at least one finger or the hand, and wherein the flexible component comprises a hole in the middle of the flexible component to associate the flexible component with the tampon.

In other embodiments, the tampon skirt apparatus further comprises at least one line of weakness in the flexible component, wherein the at least one line of weakness marks a location in the flexible component to open the flexible component to cover the at least one finger or the hand. In yet another embodiment, the tampon skirt apparatus further comprises at least one rib associated with the flexible component, wherein the at least one rib automatically unfurls the flexible component and supports the flexible component in an opened position over the at least one finger and the hand. In an embodiment, the tampon skirt apparatus further comprises at least one support ring associated with the flexible component at an edge of the flexible component, wherein the at least one support ring automatically unfurls the flexible component and supports the flexible component in an opened position over the at least one finger and the hand. In another embodiment, the tampon skirt apparatus further comprises a first flexible component stored with an $n^{th}$ flexible component for easy disbursement and association with the tampon.

It will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims.

What is claimed is:

1. A tampon, comprising:
   a flexible component associated with said tampon that unfurls to cover at least one finger or hand when inserting the tampon into a human body cavity and is separated from said tampon after the tampon is inserted into a human body cavity; and
   at least one of: a rib associated with said flexible component, wherein said at least one rib automatically unfurls said flexible component and supports said flexible component in an opened position, or a support ring associated with said flexible component at an edge of said flexible component, wherein said at least one support ring automatically unfurls said flexible component and supports said flexible component in an opened position;
   wherein said flexible component unfurls via deployment outwardly from said tampon prior to the insertion of said tampon into the human body in the form of a skirt and provides a moisture barrier as the at least one finger or hand during insertion of said tampon into the human body cavity thereby preventing menstrual discharge from contacting the at least one finger or hand during the insertion of said tampon into the human body cavity.

2. The tampon of claim 1, wherein said flexible component attaches to said tampon at at least one of an insertion end or withdrawal end of said tampon, wherein said flexible component comprises a hole in the middle of said flexible component to attach said flexible component to said at least one of an insertion end or withdrawal end of said tampon.

3. The tampon of claim 1, further comprising at least one line of weakness in said flexible component, wherein said at least one line of weakness marks a location in said flexible component to unfurl said flexible component to cover said at least one finger or said hand.

4. The tampon of claim 1, further comprising a wrapper covering said flexible component attached to said tampon, wherein said flexible component is compacted around said tampon.

5. The tampon of claim 1, wherein said flexible component is compacted around said tampon.

6. The tampon of claim 1, wherein said flexible component comprises at least one of a round shape, a circular shape, an oval shape, a square shape, and a rosebloom shape.

7. The tampon of claim 1, wherein said flexible component comprises at least one of an anaerobically degradable material, an anaerobically degradable thermoplastic polymers, polyesteramides, polyhydroxyalkoates, a film, a laminate, a shaped article, a plastic material, a fluid impervious film, a fluid repellant film, a nonwoven film, a polymeric films made of polyethylene, polypropylene, polyester, polystyrene, PET (polyethylenetherephthalate), cellophane, polyamide, poly(vinyl chloride), or ethylene-vinyl acetate copolymer, a synthetic rubber elastomer, a natural rubber elastomers, and a film having a thickness of less than about 1 mm.

8. The tampon of claim 1, wherein said tampon comprises at least one of a digital tampon, a catamenial tampon, and an applicator tampon.

9. A tampon skirt, comprising a flexible component removably attached to at least one of a tampon or tampon applicator that unfurls to cover at least one finger or hand during insertion of said tampon into a human body cavity and at least one of a rib or a support ring associated with said flexible component, wherein said at least one of the rib or the support ring enables said supporting structure to automatically unfurl and supports said flexible component in an opened position over said at least one finger and said hand, wherein said flexible component prevents menstrual discharge from contacting said at least one finger or said hand, and wherein said flexible component is detachable from said at least one of a tampon or tampon applicator upon insertion of said tampon in the human body cavity.

10. The tampon skirt of claim 9, further comprising at least one line of weakness in said flexible component, wherein said at least one line of weakness marks a location in said flexible component to open said flexible component to cover said at least one finger or said hand.

11. The tampon skirt of claim 9, wherein said flexible component is compacted around said tampon prior to use.

12. The tampon skirt of claim 9, wherein said tampon comprises at least one of a digital tampon, a catamenial tampon, and an applicator tampon.

13. A tampon, comprising a flexible component removably attached to said tampon that unfurls into the form of a skirt to cover at least one finger or hand when a user is inserting said tampon into a human cavity, wherein said flexible component prevents menstrual discharge from contacting said at least one finger or said hand, and wherein said flexible component comprises at least one of a hole in the middle of said flexible component to associate said flexible component with said tampon, at least one rib to automatically unfurl and support said flexible component in an opened position, a ring associated with said flexible component at an edge of said flexible component to automatically unfurl and support said flexible component in an opened position, and at least one line of weakness in said flexible component, wherein said at least one line of weakness marks a location in said flexible component to open said flexible component to cover said at least one finger or said hand.

14. The tampon of claim 13, wherein said flexible component further comprises at least one of an anaerobically degradable material, an anaerobically degradable thermoplastic polymers, polyesteramides, polyhydroxyalkoates, a film, a laminate, a shaped article, a plastic material, a fluid impervious film, a fluid repellant film, a nonwoven film, a polymeric films made of polyethylene, polypropylene, polyester, polystyrene, PET (polyethylenetherephthalate), cellophane, polyamide, poly(vinyl chloride), or ethylene-vinyl acetate copolymer, a synthetic rubber elastomer, a natural rubber elastomers, and a film having a thickness of less than about 1 mm.

15. The tampon of claim 13, wherein said tampon further comprises at least one of a digital tampon, a catamenial tampon, and an applicator tampon.

16. The tampon of claim 13, further comprising a first flexible component stored with an $n^{th}$ flexible component for easy disbursement and association with said tampon.

* * * * *